US011074685B2

(12) United States Patent
Peng et al.

(10) Patent No.: US 11,074,685 B2
(45) Date of Patent: Jul. 27, 2021

(54) METHOD AND SYSTEM FOR LOCALIZING IMPLANTED INTRACRANIAL ELECTRODE

(71) Applicant: National Yang Ming Chiao Tung University, Hsinchu (TW)

(72) Inventors: Syu-Jyun Peng, Hsinchu County (TW); Cheng-Chia Lee, Taipei (TW); Chien-Chen Chou, Taipei (TW); Hsiang-Yu Yu, Taipei (TW)

(73) Assignee: NATIONAL YANG MING CHIAO TUNG UNIVERSITY, Hsinchu (TW)

( * ) Notice: Subject to any disclaimer, the term of this patent is extended or adjusted under 35 U.S.C. 154(b) by 59 days.

(21) Appl. No.: 16/368,845

(22) Filed: Mar. 28, 2019

(65) Prior Publication Data

US 2020/0111207 A1 Apr. 9, 2020

(30) Foreign Application Priority Data

Oct. 4, 2018 (TW) ................................ 107135125

(51) Int. Cl.
*A61B 6/03* (2006.01)
*A61B 5/055* (2006.01)
(Continued)

(52) U.S. Cl.
CPC ............ *G06T 7/0012* (2013.01); *A61B 5/055* (2013.01); *A61B 5/24* (2021.01); *A61B 5/291* (2021.01);
(Continued)

(58) Field of Classification Search
CPC ............ A61B 2576/026; A61B 5/0035; A61B 5/0478; A61B 5/055; A61B 5/743;
(Continued)

(56) References Cited

U.S. PATENT DOCUMENTS

| 7,225,012 B1 * | 5/2007 | Susil ...................... A61B 90/36 600/414 |
| 8,014,625 B2 * | 9/2011 | Dewaele .................. G06T 7/60 382/267 |

(Continued)

FOREIGN PATENT DOCUMENTS

| CN | 1311406 C | 4/2007 |
| CN | 103932796 A | 7/2014 |

(Continued)

*Primary Examiner* — David Bilodeau
(74) *Attorney, Agent, or Firm* — CKC & Partners Co., LLC

(57) ABSTRACT

A method for localizing an intracranial electrode in a subject's brain is provided. The intracranial electrode has at least one electrode contact. The method includes: acquiring a first brain image reconstructed from first image data acquired after electrode-implantation; acquiring a second brain image reconstructed from second image data acquired before the electrode-implantation; co-registering the first brain image and the second brain image to acquire spatial transformation parameters; extracting a first coordinate of the electrode contact from the first brain image; converting the first coordinate into a second coordinate in the second brain image by using the spatial transformation parameters; co-registering the second brain image and a universal brain atlas to define functional zones in the second brain image; and defining a corresponding functional zone where the second coordinate is located. Another alternative method and a system for localizing an intracranial electrode are also provided herein.

14 Claims, 5 Drawing Sheets

(51) Int. Cl.
  *A61N 1/05*    (2006.01)
  *A61B 6/00*    (2006.01)
  *A61B 5/24*    (2021.01)
  *A61B 5/291*   (2021.01)
  *G06T 7/00*    (2017.01)
  *G06T 7/11*    (2017.01)
  *G06T 5/30*    (2006.01)
  *G06T 11/00*   (2006.01)

(52) U.S. Cl.
  CPC .............. *A61B 6/032* (2013.01); *A61B 6/463* (2013.01); *A61B 6/5247* (2013.01); *A61N 1/0534* (2013.01); *G06T 5/30* (2013.01); *G06T 7/11* (2017.01); *G06T 11/003* (2013.01); *G06T 2207/10072* (2013.01); *G06T 2207/10088* (2013.01); *G06T 2207/20048* (2013.01); *G06T 2207/30016* (2013.01)

(58) Field of Classification Search
  CPC .......... A61B 6/032; A61B 6/12; A61B 6/463; A61N 1/0529; A61N 1/0534; G06T 2207/10088; G06T 2207/20128; G06T 2207/30016; G16H 30/40
  See application file for complete search history.

(56) References Cited

U.S. PATENT DOCUMENTS

| | | | | |
|---|---|---|---|---|
| 2009/0287271 | A1* | 11/2009 | Blum | G06K 9/00885 607/45 |
| 2012/0116244 | A1* | 5/2012 | McIntyre | A61N 1/36103 600/554 |
| 2012/0271151 | A1 | 10/2012 | LaVoilette et al. | |
| 2014/0153797 | A1* | 6/2014 | Wan | G06T 7/38 382/128 |
| 2014/0350380 | A1* | 11/2014 | Eidelberg | A61B 6/037 600/410 |
| 2016/0120457 | A1 | 5/2016 | Wu et al. | |
| 2016/0144194 | A1* | 5/2016 | Roothans | A61N 1/37247 607/45 |
| 2017/0056678 | A1* | 3/2017 | Bokil | G06T 7/74 |
| 2017/0348061 | A1* | 12/2017 | Joshi | A61M 5/172 |
| 2017/0367608 | A1* | 12/2017 | Hsin | A61B 5/0042 |
| 2018/0199998 | A1* | 7/2018 | Chen | A61B 34/20 |

FOREIGN PATENT DOCUMENTS

| | | | | |
|---|---|---|---|---|
| EP | 1657681 A1 * | 5/2006 | | G06T 7/35 |
| TW | 499308 B | 8/2002 | | |
| TW | I586326 B | 6/2017 | | |
| TW | 201800054 A | 1/2018 | | |

* cited by examiner

METHOD AND SYSTEM FOR LOCALIZING IMPLANTED INTRACRANIAL ELECTRODE

CROSS-REFERENCE TO RELATED APPLICATION

This application claims priority to Taiwan Application Serial Number 107135125, filed Oct. 4, 2018, which is herein incorporated by reference in its entirety.

BACKGROUND

Field of Invention

The present disclosure relates to methods and systems for localizing intracranial electrodes.

Description of Related Art

Electrodes implanted in a subject's brain may be used to record brainwaves or emit current for stimulating changes within a subject's brain. Intracranial depth electrodes can be used to record brainwave signals; for example, stereoelectroencephalography (SEEG) is an invasive brainwave recording method commonly used in clinic at present.

SEEG was first developed by French physicians, Jean Talairach and Jean Bancaud, in the 1950s and then popularized in France and Italy. According to the previous study in Europe, SEEG can accurately record brainwaves in deep cortical and subcortical structures, and can also be used for multiple, non-continuous brain lobe lesions. Moreover, SEEG can be applied to simultaneously record brainwaves in both hemispheres. The requirement of craniotomy to place subdural grid is avoided.

SEEG electrode placement is a very complicated procedure requiring a number of processes. However, after the SEEG electrodes are placed in deep regions in the brain, the anatomical positions of more than 100 electrode contacts, the signals from more than 100 electrode contacts, and the recording of more than 168 hours are still clinically interpreted by naked eyes. This is time-consuming and labor-intensive, and qualitative and quantitative analysis of the anatomical positions of the brain is lacking. Therefore, it is desired to reduce the clinical workload and human error in determining the anatomical positions where the electrode contacts are located.

SUMMARY

The present disclosure provides a method for localizing an intracranial electrode in a subject's brain. The method includes: acquiring a first brain image reconstructed from first image data acquired after implantation of the intracranial electrode, wherein the intracranial electrode has at least one electrode contact; acquiring a second brain image reconstructed from second image data acquired before the implantation of the intracranial electrode; co-registering the first brain image and the second brain image to acquire spatial transformation parameters; extracting a first coordinate of the electrode contact from the first brain image; converting the first coordinate into a second coordinate in the second brain image by using the spatial transformation parameters; co-registering the second brain image and a universal brain atlas to define functional zones in the second brain image; and defining a corresponding functional zone where the second coordinate is located.

The present disclosure also provides a system for localizing an intracranial electrode in a subjects brain, wherein the intracranial electrode has at least one electrode contact. The system includes a computer unit and a display unit. The computer unit is configured to perform operations including acquiring a first brain image reconstructed from first image data acquired after electrode implantation; acquiring a second brain image reconstructed from second image data acquired before electrode implantation; co-registering the first brain image and the second brain image to acquire spatial transformation parameters; extracting a first coordinate of the electrode contact from the first brain image; acquiring the second coordinate in the second brain image via the first coordinate and the spatial transformation parameters; co-registering the second brain image and a universal brain atlas to define functional zones in the second brain image; and defining a corresponding functional zone where the second coordinate is located. The display unit is configured to display the electrode contact and the corresponding functional zone.

In some embodiments, the method further includes visualizing each contact and the corresponding functional zone where the contact is located.

In some embodiments, the first brain image is a computed tomography (CT) image.

In some embodiments, the second brain image is a magnetic resonance (MR) image.

In some embodiments, the step of co-registering the second brain image and the universal brain atlas to define functional zones in the second brain image comprises generating a personalized brain atlas of the subject.

In some embodiments, the electrode is a depth electrode for SEEG.

In some embodiments, the electrode is used for deep brain stimulation (DBS).

In some embodiments, the step of co-registering the first brain image and the second brain image to acquire the spatial transformation parameters comprises performing rigid body transformation.

In some embodiments, the step of extracting the first coordinate of the electrode contact from the first brain image includes segmenting the electrode contacts from the first brain image.

In some embodiments, the step of extracting the first coordinate of the electrode contact from the first brain image includes labeling the electrode contacts of the electrode in the first brain image.

In some embodiments, the step of extracting the first coordinate of the electrode contact from the first brain image includes dilating the electrode contacts in the first brain image.

In some embodiments, the method further includes resampling and reorienting the second brain image.

In some embodiments, the universal brain atlas is Brodmann area atlas.

In some embodiments, the universal brain atlas is Eve atlas.

In some embodiments, the step of co-registering the second brain image and the universal brain atlas to define functional zones in the second brain image comprises performing non-rigid body transformation.

In some embodiments, the step of co-registering the second brain image and the universal brain atlas to define functional zones in the second brain image includes generating flow fields.

In some embodiments, the step of performing the non-rigid body transformation comprises using a set of non-linear deformation parameters.

In some embodiments, the step of defining the corresponding functional zone where the second coordinate is located comprises calculating the possibility that each electrode contact is located in at least one of the functional zones.

Some embodiments of the present disclosure also provide another method for locating an intracranial electrode in a subject's brain, wherein the intracranial electrode has at least one electrode contact. The method comprising: acquiring a pre-electrode-implantation image of the subjects brain; acquiring a post-electrode-implantation image of the subject's brain; co-registering the pre-electrode-implantation image and the post-electrode-implantation image; extracting the electrode contact from the post-electrode-implantation image; acquiring a corresponding location of the electrode contact in the space of the pre-electrode-implantation image; co-registering the pre-electrode-implantation image and a universal brain atlas; defining subregions in the space of the pre-electrode-implantation image; and mapping the electrode contact and a corresponding subregion in which the electrode contact is located.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
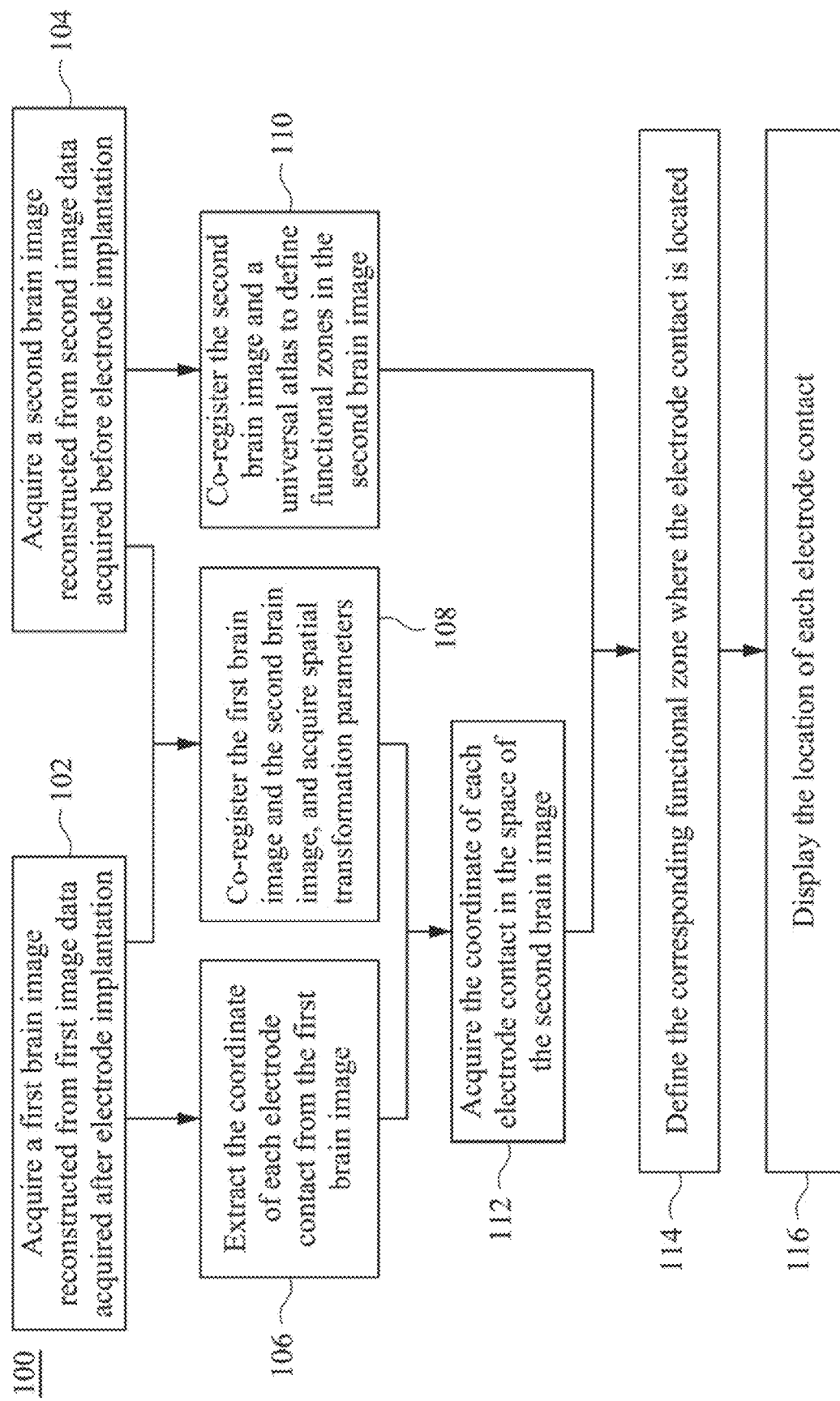
FIG. 1 is a flowchart illustrating a method for localizing intracranial electrodes in accordance with some embodiments of the present disclosure.

Reference will now be made in detail to the present embodiments of the invention, examples of which are illustrated in the accompanying drawings. Wherever possible, the same reference numbers are used in the drawings and the description to refer to the same or like parts.

The use of ordinals such as first and second does not necessarily imply a ranked sense of order, but rather may only distinguish between multiple instances of an act or structure. As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

While the embodiments or examples of the present disclosure are illustrated and described herein as a series of acts or events, it will be appreciated that the illustrated ordering of such acts or events is not to be interpreted in a limiting sense. For example, some acts may occur in different orders and/or concurrently with other acts or events apart from those illustrated and/or described herein. Further, not all illustrated acts may be required to implement one or more aspects or embodiments of the description herein, and one or more of the acts depicted herein may be carried out in one or more separate acts and/or phases.

The present disclosure can be applied in localizing electrodes implanted intracranially, e.g., SEEG electrodes or DBS electrodes. The electrodes may be strip-shaped and respectively have at least one electrode contact. SEEG electrodes can be used for localizing a specific epileptic discharge site in a subject's brain. DBS electrodes can be used in patients requiring deep brain stimulating or requiring electrode placed in the brains, such as patients with Parkinson's disease, tremor, etc.

Some embodiments of the present disclosure provide methods which can automatically map the anatomical location of the intracranial electrode and/or electrode contacts and the corresponding brain functional zones (i.e., subregions). The method can be applied to localizing electrodes in superficial cortical brain regions, lower cortical regions, white matter regions, and deep nuclear regions. Such labeling and localizing methods will contribute to the reconstruction of brain circuits and related research in the study of neurodegenerative diseases.

FIG. 1 is a flowchart illustrating method 100 for localizing an intracranial electrode in accordance with some embodiments. In step 102 of method 100, a first brain image reconstructed from first image data is acquired. The first image data are acquired after a patient receives electrode implantation. The first image data may be, for example, acquired from computed tomography (CT) scan. In some embodiments, the first brain image is a three-dimensional (3D) brain image reconstructed from image data or a plurality of two-dimensional image slices via three-dimensional reconstruction, such as a 3D CT image. The position of the electrodes or electrode contacts can then be determined in the two-dimensional (2D) or 3D images by using the shape or image characteristics (e.g., grayscale) of the objects. In some embodiments, the image has high resolution, for example, a resolution of 1 millimeter (mm) or higher, to accurately present the positions of the electrode contacts.

In step 104 of method 100, a second brain image reconstructed from second image data is acquired. The first image data are acquired before the patient receives electrode implantation. The second image data may be acquired from magnetic resonance imaging (MRI) scan. MR (magnetic resonance) image may be, for example, T1-weighted image or T2-weighted image. In some embodiments, the second brain image is a 3D image reconstructed from image data or a plurality of image slices, such as a 3D MR image. In some embodiments, the image has a high resolution, for example, a resolution of 1 mm or higher, to accurately reconstruct the brain model of the subject and determine the locations of the electrode contacts.

In step 106 of method 100, each of the coordinates of the electrode contacts is extracted from the surrounding tissue in the first brain image. The position information of the electrodes and the electrode contacts is included in the first brain image; therefore, the position of each of the electrode contacts in the coordinate system of the 3D image space can be extracted. In some embodiments, the method further includes segmenting each of the electrode contacts and extracting the coordinates of the centroid of each of the electrode contacts.

In step 108 of method 100, the first brain image and the second brain image are co-registered, and corresponding spatial transformation parameters were acquired. The registration of medical images is a spatial transformation to find a spatial or anatomical correspondence between two images. After co-registration, the corresponding spatial transformation parameters between the first brain image and the second brain image is obtained. In some embodiments, the co-registration is performed via using rigid body transformation. For example, by using rigid body transformation, the first brain image is aligned with the second brain image and generate a transformation matrix; then, the centroid coordinates of the intracranial electrode contacts can be converted into the coordinates in the space of the second brain image through the transformation matrix.

In step 110 of method 100, the second brain image and a universal brain atlas are co-registered, and functional zones in the second brain image are defined.

In a universal brain atlas (e.g., Brodmann brain atlas, Eve atlas, Automated Anatomical Labeling digital human brain atlas, etc.), the 3D brain structure is parcelled into many functional zones. A set of universal brain atlas is often constructed from the average results of a certain number of people; however, the head shape and brain volume of various subjects are different. In practice, it is not possible to apply a universal brain atlas into specific subjects directly, and the function for a region of a subject's brain is determined or predicted by experienced experts. Therefore, at present the relevant auxiliary display technology is still lacking.

In some embodiments, after the second brain image is registered with the universal brain atlas, the personalized brain atlas of the subject is generated. The second brain image, a pre-electrode-implantation image, has the same or corresponding coordinate system and the same number of voxels as the personalized brain atlas; therefore, the voxels with the same coordinate (i.e., the corresponding voxels) respectively in the two images correspond to the same physical location in the subject's brain.

Each of the functional zones in the personalized brain atlas respectively corresponds to each of the functional zones of the universal brain atlas. Therefore, the spatial range or the 3D coordinate range of each corresponding functional zone in the second brain image can be obtained.

In some embodiments, the second brain image is co-registered with the universal brain atlas via performing non-rigid body transformation. In some embodiments, image registering programs, such as Diffeomorphic anatomical registration through Exponential Lie Algebra (DARTEL) module can be used. In co-registering the second brain image and the universal brain atlas, DARTEL is used to generate a set of non-linear deformation parameters for acquiring the personalized brain atlas.

In step 112 of method 100, the coordinate of each of the electrode contacts in the space of the second brain image is acquired. The corresponding coordinate of each of the electrode contacts in the space of the second brain image can be acquired based on the coordinate of each of the electrode contacts in the first brain image and the spatial transformation parameters between the first brain image and the second brain image. In some embodiments, the coordinate of the centroid of each of the electrode contacts in the first bran image is converted into the corresponding coordinate in the space of the second brain image via the transformation matrix obtained in the co-registration process.

In step 114 of method 100, the functional zone(s) where each of the electrode contacts located is defined. In some embodiments, since the respective voxels belonging to which functional zones can be identified, and the voxel coordinates of the electrode contact in the second brain image can also be identified; then the corresponding functional zone where the voxels of the electrode contact are located can be calculated.

In some embodiments, the possibility of the functional zone where the electrode contact is located in the personalized brain atlas can be calculated by using connectivity of 26-connected neighborhood for three dimensions to determine the centroid of the electrode contact. Then, the possible corresponding functional zone(s) wherein the electrode contact is located can be labeled.

In step 116 of method 100, the location for each of the electrode contacts is visualized to present each of the electrode contacts and the corresponding functional zone(s) where the electrode contact is located. For example, the location of each of the contacts is displayed in a personalized brain atlas. In some embodiments, in step 116, the method further includes outputting the voxel coordinates of each functional zone and each electrode in the personalized brain atlas, and the voxels belonging to different functional zones and different electrodes can be respectively labeled with distinct colors. Therefore, the locations for each of the electrode contacts and each of the corresponding functional zones where the electrode contacts are located can be displayed in 2-D or 3-D images.

Figure 2:
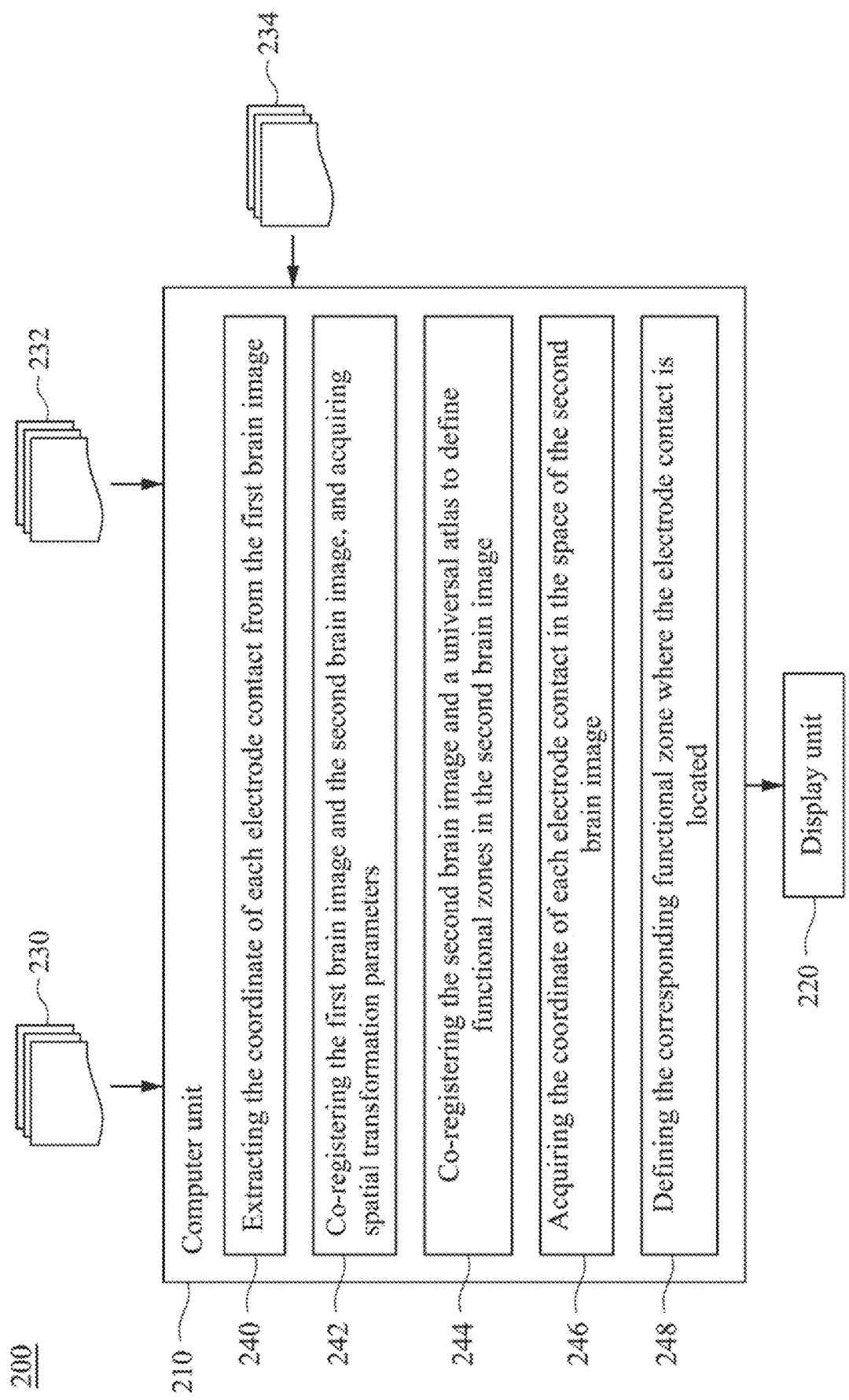
FIG. 2 is a schematic diagram illustrating a system for localizing intracranial electrodes in accordance with some embodiments of the present disclosure.

FIG. 2 shows system 200 for localizing intracranial electrodes. System 200 includes a computer unit 210 and a display unit 220. The computer unit 210 is configured to perform operations of image processing. In FIG. 2, the computer unit 210 acquires first brain image 230, which is reconstructed from first image data acquired after the subject receives electrode implantation. Computer unit 210 also acquires second brain image 232, which is reconstructed from second image data acquired before the subject receives electrode implantation. The operations for computer unit 210 further comprise operation 240, 242, 246, and 248. Operation 240 is extracting the coordinate of each of the electrode contacts from the first brain image. Operation 242 is co-registering first brain image 230 with second brain image 232 and acquiring corresponding spatial transformation parameters. Operating 244 is co-registering second brain image 232 with universal brain atlas 234 to define the functional zones in the second brain image. Operating 246 is acquiring the coordinate of each of the electrode contacts in the space of second brain image 232. Operation 248 is defining the functional zone where each of the electrode contacts is located.

Display unit 220 of system 200 is configured to display the location of each of the electrode contacts to show each of the electrode contacts and the corresponding functional zone(s). Therefore, the physicians or image analysts can directly interpret the corresponding functional zones where the electrode contacts are located.

The following disclosure relates to methods for localizing SEEG electrodes for epilepsy patients in accordance with some embodiments.

Epilepsy is a neurological disorder with abnormal discharge of brain cells due to brain lesions. Patients often suffer from declining life quality because of repeated and unpredictable seizures, and the work of the patients is affected. Severe patients are at high risk of life-threatening.

The prevalence of epilepsy is 1%, regardless of age, gender and socioeconomic status. About 200-250 thousand people in Taiwan suffer from seizures. The treatment of epilepsy is firstly based on anti-epileptic drugs, and 70% of epilepsy patients can achieve no occurrence of seizures or effective control by taking the drugs. About 30% of patients are unable to achieve effective control of epilepsy, although they are treated with multiple anti-epileptic drugs. The syndrome is called drug-resistant epilepsy, and surgery can be considered for epilepsy treatment.

However, not every patient with drug-resistant epilepsy is suitable for epilepsy surgery. The patients require a complete preoperative evaluation to accurately localize the epileptogenic zone in order to effectively improve the success rate of epilepsy surgery and eradicate epilepsy. Common non-invasive preoperative assessment examinations, such as long-term video-electroencephalography (V-EEG), brain MRI, and Positron emission tomography (PET), and neuropsychological cognitive and memory function assessment, can be used to identify the origin of seizure, brain structural abnormalities, brain metabolic abnormalities, the degree of the high cognitive function affected by epilepsy, etc. However, satisfactory results may still not be obtained through such above examinations, so that an invasive brainwave recording is required to explore the deeper potential electric voltage/field changes in the brain. SEEG is commonly used clinically for invasive brainwave recording. At present, SEEG electrode placement has become an important surgical method for finding the epileptogenic zone in a brain for many epilepsy centers in the world.

Most patients have patterned epilepsy onset type, indicating that a consensus epilepsy source and delivering network routes and regions exist within these patients. Therefore, establishing an epilepsy circuit in a brain is an urgent need for clinicians.

Before implantation of SEEG electrodes, the personalized plan for each patient is made based on medical history, preoperative evaluation, location, and image findings.

In some embodiments, on the morning of the surgery day, SEEG frame (e.g., leksell frame) is attached to the patient, and MR images are taken in MRI room for positioning the electrodes. During the period when the neurosurgeon is planning to position the electrodes, the patients can be sent to the operating room for anesthesia. After the target area is determined via SEEG planning software (e.g., sugiPlan, elekta, etc.), electrodes respectively with different length, different contact intervals, and different numbers of contacts can be used to probe the target area (i.e., the epileptogenic zone).

In some embodiments, the patient receives general anesthesia, and the positioning procedure is initiated after disinfection. A depth electrode is placed through drilling a burr hole on a skull by using twist drill, burning the dura mater by using a unipolar electric burner, placing the electrode at a predetermined depth and position, and locking the nut securely to the bolt. Each electrode placement can be checked by real-time examination through X-ray photography (such as C-arm x-ray) to avoid electrode bending, too much depth, or insufficient depth.

After surgery, the patient is sent to the imaging room for MRI or CT. Then, after the location of each of the electrodes is confirmed, the patient is sent to the epilepsy video room for 7-14 days for intracranial brainwave recording.

Figure 3:
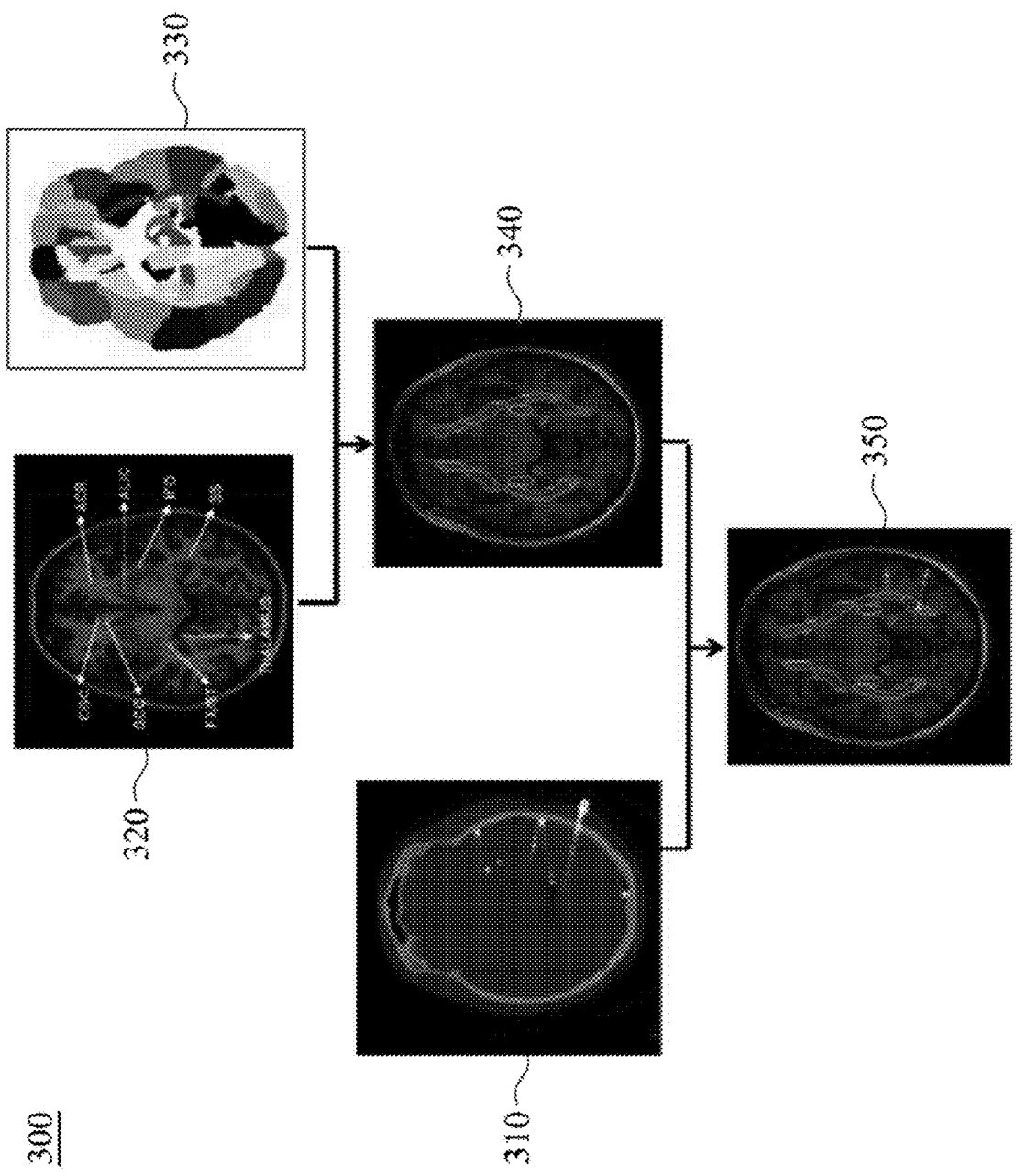
FIG. 3 is a flowchart illustrating some steps of a method for localizing SEEG electrodes in accordance with some embodiments of the present disclosure.

Referring to FIG. 3, which illustrates a flowchart for localizing SEEG electrodes according to some embodiments. For simplicity and clarity, the image slices (2D images) with the same orientation and in close planes after the registration process are used to illustrate some steps of the method. The electrode contacts, the anatomical positions, and the corresponding functional zones are presented in FIG. 3.

Image 310 of method 300 is a post-electrode-implantation CT image showing the contour of the brain and the electrode contacts of the implanted electrodes. Image 320 of method 300 is a pre-electrode-implantation MRI image, and some specific nerve fiber bundle blocks (i.e., functional zones) are labeled, such as GCC represents Cingulum (cingulate gyrus), GCC represents of Genu of corpus callosum, FX/ST represents fornix (cres)/stria terminalis, ACR represents anterior corona radiate, ALIC represents anterior limb of internal capsule, IFO represents inferior fronto-occipital fasciculus, and SS represents sagittal stratum.

Image 330 of method 300 is a universal brain atlas, wherein the different colors (or grayscale degrees) indicate different brain functional zones.

Images 320 and 320 are co-registered and fused; then image 340 is acquired. The regions circled by the gray line indicate these regions corresponding to the functional zones in image 320.

Image 310 is combined with image 340, and then the merged image 350 is acquired. Image 350 simultaneously displays the positions of the electrode contacts and the positions of the functional zones.

The following disclosure describes the methods via different universal brain atlases for localizing SEEG depth electrodes in an epilepsy patient, and more details for image processing are provided, particularly in localizing electrode contacts in a CT image, and in acquiring a personalized brain atlas. However, these specific details are not intended to limit the scope of the disclosure.

Figure 4:
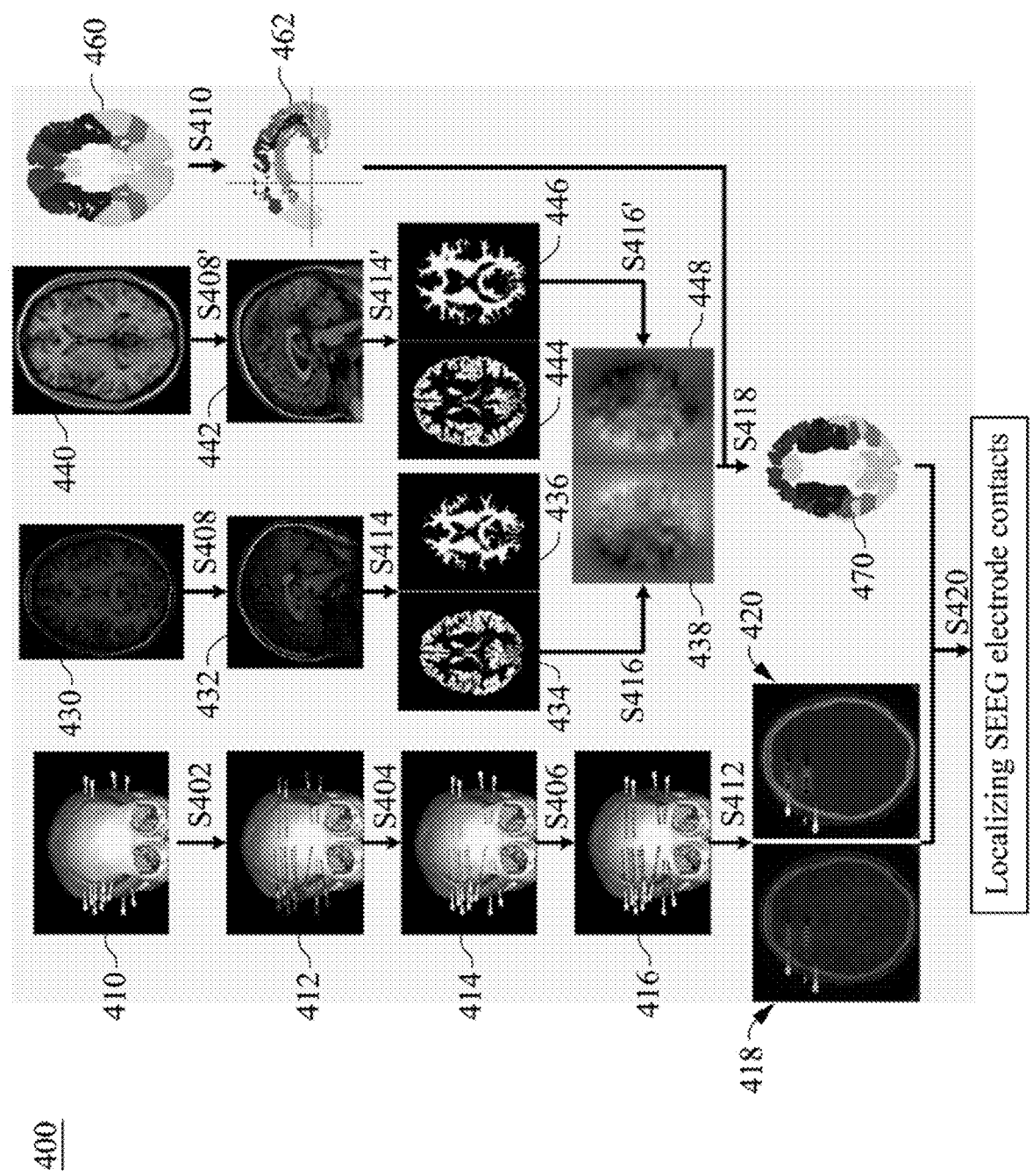
FIG. 4 is a flowchart illustrating a method for localizing SEEG electrodes via using Brodmann area atlas in accordance with some embodiments of the present disclosure.

Referring to FIG. 4, which shows method 400 for localizing SEEG electrodes via Brodmann area atlas. In FIG. 4, 2-D image slices of an epilepsy patient are used to illustrate the processes for localizing electrodes. In this example, 14 electrodes were implanted into the skull of the patient, each electrode has 8 to 10 electrode contacts, and there is a total of 116 electrode contacts.

Brodmann area atlas includes 182 2-D image slices. The personalized brain atlas is acquired based on a pre-electrode-implantation MR image and Brodmann area atlas. Then, the coordinate ranges of different functional zones in the space of MR image can be obtained.

Image Acquisition

Figure 5:
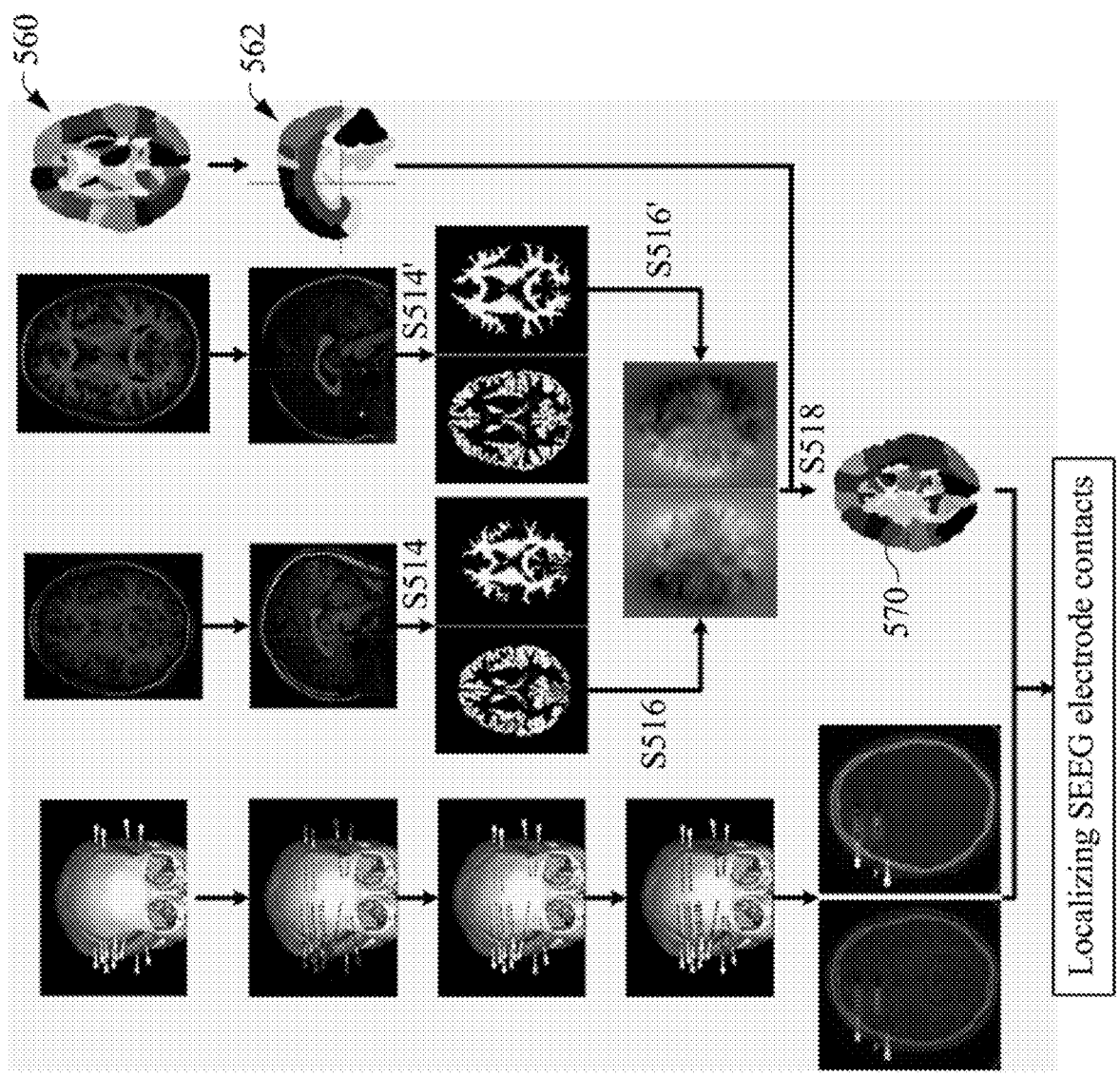
FIG. 5 is a flowchart illustrating a method for localizing SEEG electrodes via using Eve atlas in accordance with some embodiments of the present disclosure.

With respect to the CT image shown in FIGS. 4 and 5, the post-electrode-implantation CT scan was performed within 24 hours of implantation using the following technical parameters: 64 slices; rotation duration of 1 second with coverage of 16 cm per rotation; 60 kW generator (512×512 matrix), 120 KV, 301 mAs; axial slice thickness of 1 mm.

With respect to the MR image shown in FIGS. 4 and 5, the pre-electrode-implantation MRI data of the subject were obtained on a 1.5T MRI machine (GE, Signa HDxt) equipped with eight-channel phased array head coil. The MR image data were taken along the axial plane using a fast spoiled gradient-recalled echo sequence (TR/TE/TI=10.02/4.28/0 ms, flip angle of 15°, matrix of 256×256, bandwidth of 31.2 kHz, field of view measuring 256×256 mm, and axial slice thickness of 1.0 mm). Then, a high-resolution 3-D T1-weighted MR image was reconstructed from the MR image data.

In method 400 in FIG. 4, Image 410 is a post-electrode-implantation CT image. In step S402, the electrode contacts are extracted. In a CT image, the metal portion of the electrode is brighter than the soft tissue and most of the hard tissue. Extracting SEEG electrode contacts from surrounding tissue in the post-electrode-implantation CT image can be achieved rapidly by setting a threshold range that encompasses the grayscale voxels that represent the target contacts, then effectively isolating these voxels into an object of interest. This step can be carried out automatically or semi-automatically. Some manual cleaning may be required to remove non-contact voxels, such as fractional leads, bones or scalp.

Image 412 in method 400 shows the positions of the various extracted electrode contacts of the intracranial electrodes. Then, in step S404, each of the electrode contacts is labeled. The connected-component labeling of each of the electrode contacts is carried out by using the connectivity of 26-connected neighborhood for three dimensions. The voxels belonging to the electrode contacts are displayed in different colors (or different grayscale degrees) to easily identify the locations of the electrode contacts in the brain.

The colored dots (or gray dots) in image 410 in method 400 are the electrode contacts after image segmentation process. Then, in step S406, a dilating operation of the electrode contacts is performed. The dilating operation of morphology is performed a dilation on the binary volume of SEEG electrode contacts using the 3×3×3 box structuring element. Image 416 in method 400 is an image with dilated electrode contacts.

Images 430 and 440 in method 400 are different image slices of a 3D pre-electrode-implantation MR image. In steps S408 and S408', the image is registered, including resampling and reorientating the MR image. The MR image is resampled to 1×1×1 mm$^3$ and reoriented the mm coordinate of the anterior commissure to match the origin (0, 0, 0). Images 432 and 442 are image slices of the registered MR image.

Image 460 in method 400 is an image slice of Brodmann area atlas. In step S410, image reorientation is performed, and image 462 is an image slice of the reoriented Brodmann area atlas. The cross symbols in images 432, 442, and 462 are reference marks for image display.

In step S412 in method 400, co-registration is performed to obtain the centroid position of each of the electrode contacts in the space of the MR image. In step S412, the CT image is a source image, and the MRI image is a reference image, allowing the CT image data to be transformed to the MR image space. The post-electrode-implantation CT image with dilated electrode contact objects is registered to the resampled and reoriented pre-electrode-implantation MRI image by 3-D voxel registration based on the normalized mutual information method. Then, the centroid of each of the electrode contacts in the pre-electrode-implantation MR image is obtained. Images 418 and 420 are merged images after co-registration of the CT image and the MR image.

In steps S414 and S414' of method 400, imported tissue class images are generated. The New Segment option of Statistical Parametric Mapping 8 (SPM8, Wellcome Department of Cognitive Neurology, London, UK, http://www.fil.ion.ucl.ac.uk/spm/) software package is applied on the registered and reoriented pre-implantation MR image of the subject and Brodmann area atlas to generate the imported tissue class image sets, respectively, i.e., the imported gray matter images (e.g. images 434 and 444) and the imported white matter images (images 436 and 446).

In steps S416 and S416' of method 400, flow fields are generated. The imported tissue class image sets of the subject and Brodmann area atlas are utilized to generate backward and forward flow fields as well as a series of template images through the DARTEL (Diffeomorphic Anatomical Registration through Exponential Lie Algebra) option embedded in SPM8. Images 438 and 448 are template images.

In step S418 of method 400, image warping is performed. The Brodmann area atlas is warped to match the shape of the subject based on the forward and backward flow fields to obtain personalized brain atlas through Deformation option of SPM8.

In step S420 in method 400, the electrode contacts are localized. SEEG electrode contacts are localized using a gradual approach reflecting the composition of tissue surrounding the contact centroid. The proportion of different anatomical structural MRI voxels contiguous to the centroid of each contact was estimated based on identified functional zones from the personalized anatomical atlas. The anatomy mix surrounding each electrode contact was defined using the proximal anatomy probability in a 3×3×3 mm$^3$ volume surrounding the centroid of the electrode contact (i.e., 26 voxels).

In step S420, the electrode contacts can be displayed in the brain image. FreeSurfer can be used to reconstruct a 3D model of cortical surfaces based on the registered and reoriented pre-electrode-implantation MR image. MATLAB program (The MathWorks Inc., Natick, Mass.) can be used to embed SEEG electrode contact locations within the reconstructed 3D model of the cortex.

Table 1 below shows the positions of the respective electrode contacts of three electrodes (RF1, RF2, and RF3), among others, in the subject's brain in FIG. 4.

TABLE 1

| Electrode contact | No. of functional zone | Possibility | No. of functional zone | Possibility | No. of functional zone | Possibility |
|---|---|---|---|---|---|---|
| RF1 01 | 32 | 100% | | | | |
| RF1 02 | 32 | 100% | | | | |
| RF1 03 | 46 | 93% | 1000 | 7% | | |
| RF1 04 | 46 | 100% | | | | |
| RF1 05 | 46 | 100% | | | | |
| RF1 06 | 45 | 74% | 46 | 26% | | |
| RF1 07 | 45 | 56% | 46 | 44% | | |
| RF1 08 | 1000 | 52% | 45 | 33% | 46 | 15% |
| RF2 01 | 10 | 81% | 11 | 19% | | |
| RF2 02 | 10 | 70% | 11 | 30% | | |
| RF2 03 | 11 | 100% | | | | |
| RF2 04 | 47 | 100% | | | | |
| RF2 05 | 47 | 100% | | | | |
| RF2 06 | 47 | 63% | 45 | 37% | | |

TABLE 1-continued

| Electrode contact | No. of functional zone | Possibility | No. of functional zone | Possibility | No. of functional zone | Possibility |
|---|---|---|---|---|---|---|
| RF2 07 | 45 | 100% | | | | |
| RF2 08 | 45 | 100% | | | | |
| RF2 09 | 45 | 93% | 1000 | 7% | | |
| RF2 10 | 1000 | 100% | | | | |
| RF3 01 | 32 | 100% | | | | |
| RF3 02 | 32 | 100% | | | | |
| RF3 03 | 9 | 100% | | | | |
| RF3 04 | 9 | 52% | 46 | 48% | | |
| RF3 05 | 46 | 96% | 9 | 4% | | |
| RF3 06 | 46 | 100% | | | | |
| RF3 07 | 45 | 52% | 46 | 48% | | |
| RF3 08 | 45 | 67% | 1000 | 33% | | |

1000 indicates that the electrode contacts may be not located within the functional zones of the atlas.

The 100% possibility of the functional zone indicates the electrode contact is most likely located in this functional zone. When there are significant possibilities for an electrode contact in a plurality of functional zones, the electrode contact may be located close to the boundary between these functional zones.

The Brodmann areas define cerebral cortex into a series of anatomical regions based on the cytoarchitectural organizations. Brodmann areas were originally defined and numbered by the German anatomist Korbinian Brodmann. Brodmann areas initially included 52 regions per hemisphere. At present, some of the Brodmann areas have been subdivided; for example, Zone 23 is subdivided into 23a and 23b. Such of brain functional zones is related to many clinical manifestations of diseases, especially epilepsy. The onset pattern of epilepsy has a great correlation with specific areas which are parcellated according to brain function or cytoarchitectural organization. In addition, the current plans for epilepsy surgery, such as the surgery way, the resection range, etc., are also closely related to Brodmann area parcellation. Therefore, using Brodmann area atlas to localize SEEG electrode is in line with both clinical needs and the communication between neuroscientists.

Referring to FIG. 5, which shows method 500 for localizing SEEG depth electrodes according to one embodiment of the present disclosure.

Method 500 in FIG. 5 is similar to method 400 in FIG. 4, except that the universal brain atlas used in method 500 is Eve atlas. In method 500 in FIG. 5, image 560 is an image slice of Eve atlas. Eve 562 is an image slice of reorientated Eve atlas. In steps S514 and S514', similar to steps S414 and S414' in FIG. 4, the imported tissue class images are generated from resampled and reoriented pre-electrode-implantation MRI image and the reoriented Eve atlas to generate the imported tissue class image sets, respectively, i.e., the imported gray matter images and the imported white matter images. In steps S516 and S516', similar to steps S416 and S416' in FIG. 4, a series of template images of backward and forward flow fields are generated based on the imported tissue class images and Eve atlas. In step S518, the White Matter Parcellation Map of Eve atlas is warped to match the shape of the subject based on the forward and backward flow fields to obtain personalized brain atlas through Deformation option of SPM8. Image 570 is an image slice of the personalized brain atlas based on the pre-electrode-implantation MR image and Eve atlas.

Table 2 below shows the positions of the respective electrode contacts of three electrodes (RF1, RF2, and RF3), among others, in the subject's brain in FIG. 4.

TABLE 2

| Electrode contact | No. of functional zone | Possibility | No. of functional zone | Possibility | No. of functional zone | Possibility |
|---|---|---|---|---|---|---|
| RF1 01 | 68 | 100% | | | | |
| RF1 02 | 68 | 100% | | | | |
| RF1 03 | 69 | 89% | 68 | 11% | | |
| RF1 04 | 69 | 100% | | | | |
| RF1 05 | 69 | 100% | | | | |
| RF1 06 | 69 | 100% | | | | |
| RF1 07 | 69 | 100% | | | | |
| RF1 08 | 69 | 52% | 1000 | 48% | | |
| RF2 01 | 89 | 89% | 105 | 11% | | |
| RF2 02 | 102 | 78% | 89 | 11% | 1000 | 11% |
| RF2 03 | 102 | 100% | | | | |
| RF2 04 | 102 | 56% | 70 | 33% | 69 | 11% |
| RF2 05 | 70 | 100% | | | | |
| RF2 06 | 70 | 93% | 69 | 7% | | |
| RF2 07 | 70 | 100% | | | | |
| RF2 08 | 70 | 100% | | | | |
| RF2 09 | 1000 | 89% | 70 | 11% | | |
| RF2 10 | 1000 | 100% | | | | |
| RF3 01 | 68 | 100% | | | | |
| RF3 02 | 68 | 100% | | | | |

TABLE 2-continued

| Electrode contact | No. of functional zone | Possibility | No. of functional zone | Possibility | No. of functional zone | Possibility |
|---|---|---|---|---|---|---|
| RF3 03 | 68 | 100% | | | | |
| RF3 04 | 68 | 100% | | | | |
| RF3 05 | 69 | 100% | | | | |
| RF3 06 | 69 | 100% | | | | |
| RF3 07 | 69 | 100% | | | | |
| RF3 08 | 69 | 100% | | | | |

1000 indicates that the electrode contacts may be not located within the functional zones of the atlas.

In recent years, because of the use of SEEG, epilepsy network research is not limited to gray matter. The use of brain atlas (e.g., Eve atlas) containing parcellated functional zones of the cerebral cortex, nerve fiber bundles, and deep gray matter will contribute to the exploration of the white matter region. Eve atlas (also called JHU-MNI-ss atlas) is based on a single-subject data. There are co-registered T1-weighted image, T2 weighted images, and white matter parcellation map (WMPM). Once an image of interest is normalized to coordinate system of Eve atlas, the WMPM can be superimposed for anatomical definition or automated segmentation. The parcellation of the Brodmann area atlas has made a detailed classification of areas of the gray matter, especially the functional zones, while the Eve atlas further parcellates the nerve fiber bundles and the gray matter of the deep brain, which are lacking in Brodmann area atlas. It is integrated and comprehensive to combine Brodmann area atlas and Eve atlas for use in automatic localizing SEEG depth electrodes.

Because SEEG has deep, dense, multi-channel characteristics, it is suitable for studying the origin and delivering of epilepsy networks, regardless of during ictal or interictal period. When SEEG is used for localizing the anatomical location of abnormal epileptic discharges in epilepsy patients, the locations of depth electrodes can be automatically mapped, and the ways for identifying functional zones and anatomical positions of the epileptogenic zone in patients can be standardized. Further, the method for automatically localizing SEEG depth electrodes can be used to more understand the roles of respective functional zones in a circuit of epileptic onset.

In some embodiments, the method further includes visualizing electrode contacts in a personalized brain atlas. Therefore, the location for each of the electrode contacts and the corresponding functional zones can be displayed. The physicians can directly interpret the 3D structure of the brain where the electrodes are located, without using speculative methods. This is beneficial to the condition and surgical needs of the subjects.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method for localizing an intracranial electrode in a brain of a subject, the method comprising:
   acquiring a first brain image reconstructed from first image data acquired after implantation of the intracranial electrode, wherein the intracranial electrode has at least one electrode contact, and the first brain image is a post-electrode-implantation computed tomography (CT) image;
   acquiring a second brain image reconstructed from second image data acquired before the implantation of the intracranial electrode, wherein the second image is a pre-electrode-implantation MR image;
   co-registering the post-electrode-implantation CT image and the pre-electrode-implantation MR image to acquire spatial transformation parameters, wherein the step comprises performing rigid body transformation;
   extracting a first coordinate of the electrode contact from the post-electrode-implantation CT image;
   converting the first coordinate into a second coordinate in the pre-electrode-implantation MR image by using the spatial transformation parameters;
   co-registering the pre-electrode-implantation MR image and a universal brain atlas to define functional zones in the pre-electrode-implantation MR image; and
   defining a corresponding functional zone where the second coordinate is located.

2. The method of claim 1, further comprising visualizing the electrode contact and the corresponding functional zone.

3. The method of claim 1, wherein the step of co-registering the pre-electrode-implantation MR image and the universal brain atlas to define the functional zones in the pre-electrode-implantation MR image comprises:
   generating a personalized brain atlas of the subject.

4. The method of claim 1, wherein the intracranial electrode is a SEEG electrode or a deep brain stimulation (DBS) electrode.

5. The method of claim 1, wherein the step of extracting the first coordinate of the electrode contact from the post-electrode-implantation CT image comprises:
   segmenting the electrode contact in the post-electrode-implantation CT image.

6. The method of claim 1, wherein the step of extracting the first coordinate of the electrode contact from the post-electrode-implantation CT image comprises:
   labeling the electrode contact in the post-electrode-implantation CT image.

7. The method of claim 1, wherein the step of extracting the first coordinate of the electrode contact from the post-electrode-implantation CT image comprises:
   dilating the electrode contact in the post-electrode-implantation CT image.

8. The method of claim 1, further comprising: resampling and reorienting the pre-electrode-implantation MR image.

9. The method of claim 1, wherein the universal brain atlas is Brodmann area atlas or Eve atlas.

10. The method of claim 1, wherein the step of co-registering the second brain pre-electrode-implantation MR image and the universal brain atlas to define the functional zones in the pre-electrode-implantation MR image comprises:
performing non-rigid body transformation.

11. The method of claim 10, further comprising:
generating flow fields based on the pre-electrode-implantation MR image.

12. The method of claim 10, wherein performing the non-rigid body transformation comprises:
using a set of non-linear deformation parameters.

13. The method of claim 1, wherein the step of co-registering the pre-electrode-implantation MR image and the universal brain atlas to define the functional zones in the pre-electrode-implantation MR image comprises:
calculating a possibility of the electrode contact locating in at least one of the functional zones.

14. A system for localizing an intracranial electrode in a brain of a subject, wherein the intracranial electrode has at least one electrode contact, the system comprising:
a computer unit configured to perform operations comprising:
acquiring a first brain image reconstructed from first image data acquired after implantation of the intracranial electrode, wherein the first brain image is a post-electrode-implantation computed tomography (CT) image;
acquiring a second brain image reconstructed from second image data acquired before the implantation of the intracranial electrode, and the second image is a pre-electrode-implantation MR image;
co-registering the post-electrode-implantation CT image and the pre-electrode-implantation MR image to acquire spatial transformation parameters, wherein the operation comprises performing rigid body transformation;
extracting a first coordinate of the electrode contact from the post-electrode-implantation CT image;
acquiring a second coordinate in the pre-electrode-implantation MR image via the first coordinate and the spatial transformation parameters;
co-registering the pre-electrode-implantation MR image and a universal brain atlas to define functional zones in the pre-electrode-implantation MR image; and
defining a corresponding functional zone where the second coordinate is located; and
a display unit configured to display the electrode contact and the corresponding functional zone.

* * * * *